(12) United States Patent
Suzuki et al.

(10) Patent No.: US 7,341,848 B2
(45) Date of Patent: Mar. 11, 2008

(54) ISOMALTOSE SYNTHASE-KNOCKOUT MICROORGANISM BELONGING EUMYCOTA

(75) Inventors: Kanako Suzuki, Tokyo (JP); Norihiro Tsukagoshi, Nagoya (JP)

(73) Assignee: Amano Enzyme Inc., Nagoya-shi (JP)

( * ) Notice: Subject to any disclaimer, the term of this patent is extended or adjusted under 35 U.S.C. 154(b) by 0 days.

(21) Appl. No.: 10/532,064

(22) PCT Filed: Oct. 20, 2003

(86) PCT No.: PCT/JP03/13353

§ 371 (c)(1),
(2), (4) Date: Jan. 12, 2006

(87) PCT Pub. No.: WO2004/038017

PCT Pub. Date: May 6, 2004

(65) Prior Publication Data

US 2006/0234338 A1    Oct. 19, 2006

(30) Foreign Application Priority Data

Oct. 23, 2002  (JP)  .............................. 2002-307922

(51) Int. Cl.
*C12P 21/00* (2006.01)
*C12N 1/15* (2006.01)

(52) U.S. Cl. .................... 435/69.1; 435/254.3

(58) Field of Classification Search ...................... None
See application file for complete search history.

(56) References Cited

FOREIGN PATENT DOCUMENTS

| JP | 62-272988 | 11/1987 |
| JP | 63-216493 | 9/1988 |

OTHER PUBLICATIONS

Kato et al., Curr. Genet. (2002) 42:43-50.*
Kato, M., et al. "An *Aspergillus nidulans* nuclear protein, AnCP, involved in enhancement of Taka-amylase A gene expression, binds to the CCAAT-containing *taaG2*, *amdS*, and *gatA* promoters;" *Mol Gen Genet*, 254, pp. 119-126. (1997).

Tsukagoshi, N., et al. "Isolation of a cDNA encoding *Aspergillus oryzae* Taka-amylase A: evidence for multiple related genes;" *Gene*, 84, pp. 319-327. (1989).
Ballance, D. J., et al. "Development of a high-frequency transforming vector for *Aspergillus nidulans;*" *Gene*, 36, pp. 321-331. (1985).
Cullen, D., et al. "Controlled Expression and Secretion of Bovine Chymosin in *Aspergillus nidulans;*" *Bio/Technology*, vol. 5, pp. 369-376. (Apr. 1987).
Kato, M., et al.; "No Factors Except for the Hap Complex increase the Taka-amylase A Gene Expression by Binding to the CCAAT Sequence in the Promoter Region;" *Biosci.Biotechnol. Biochem.*, vol. 65, No. 10, pp. 2340-2342 (2001).
Tani, S., et al.; "In Vivo and in Vitro Analyses of the AmyR Binding Site of the *Aspergillus nidulans agdA* Promoter; Requirement of the CGG Direct Repeat for Induction and High Affinity Binding of AmyR;" *Biosci.Biotechnol. Biochem.*, vol. 65, No. 7, pp. 1568-1574 (2001).
N. Kato, et al.; "Isomaltose formed by α-glucosidases triggers amylase induction in *Aspergillus nidulans;*" *Curr. Genet.*, vol. 42; No. 1; Sep. 2002; pp. 43-50.
M. Kato, et al.; "No Factors Except for the Hap Complex increase the Taka-amylase A Gene Expression by Binding to the CCAAT Sequence in the Promoter Region;" *Biosci.Biotechnol.Biochem.*; vol. 65; No. 10; 2001; pp. 2340-2342.
S. Tani, et al; "In Vivo and in Vitro Analyses of the AmyR Binding Site of the *Aspergillus nidulans agdA* Promoter; Requirement of the CGG Direct Repeat for Induction and High Affinity Binding of AmyR.;" *Biosci.Biotechnol.Biochem.*; vol. 65; No. 7; 2001; pp. 1568-1574.

* cited by examiner

*Primary Examiner*—Nancy Vogel
(74) *Attorney, Agent, or Firm*—Edwards Angell Palmer & Dodge LLP

(57) ABSTRACT

It is intended to provide a host microorganism whereby the expression of a gene encoding a target protein can be effectively elevated in the case of transferring the gene. It is also intended to provide a transformant whereby a target protein can be produced at a high efficiency. It is further intended to provide a production process whereby a target protein can be produced at a high productivity. A microorganism which belongs to *Eumycota* and lacks the major isomaltose synthase. A gene encoding a target protein is transferred into the microorganism to give a transformant. Then the transformant is cultured under conditions allowing the expression of the transferred gene to thereby produce the protein.

4 Claims, 4 Drawing Sheets

Fig.1

```
  1 GAATTCATGG TGTTTTGATC ATTTTAAATT TTTATATGGC GGGTGGTGGG CAACTCGCTT  60
 60 CCGGGCAACT CGCTTACCGA TTACGTTAGG GCTGATATTT ACGTAAAAAT CGTCAAGGGA 120
121 TGCAAGACCA AAGTAGTAAA ACCCCGGAGT CAACAGCATC CAAGCCCAAG TCCTTCACGG 180
181 AGAAACCCCA GCGTCCACAT CACGAGCGAA GGACCACCTC TAGGCATCGG ACGCACCATC 240
241 CAATTAGAAG CAGCAAAGCG AAACAGCCCA AGAAAAAGGT CGGCCCGTCG GCCTTTTCTG 300
301 CAACGCTGAT CACGGGCAGC GATCCAACCA ACACCCTCCA GAGTGACTAG GGGCGGAAAT 360
361 TTAAAGGGAT TAATTTCCAC TCAACCACAA ATCACAGTCG TCCCCGGTAT TGTCCTGCAG 420
421 AATGCAATTT AAACTCTTCT GCGAATCGCT TGGATTCCCC GCCCCTGGCC GTAGAGCTTA 480
481 AAGTATGTCC CTTGTCGATG CGATGTATCA CAACATATAA ATACTAGCAA GGGATGCCAT 540
541 GCTTGGAGGA TAGCAACCGA CAACATCACA TCAAGCTCTC CCTTCTCTGA ACAATAAACC 600
601 CCACAGAAGG CATTT                                                   615
``` taaG2 : Taka-amylase A gene
argB : ornithine carbomoyltransferase gene (selection marker)
taaM : Taka-amylase gene including modified promoter

Fig.4

| promoter | production amount of amylase (mg/L) | | | | | |
|---|---|---|---|---|---|---|
| | starch | | | maltose | | |
| | ABPU1 | ΔagdB | ABPU1/ΔagdB | ABPU1 | ΔagdB | ABPU1/ΔagdB |
| Taa | 68 | 397 | 5.8 | 81 | 572 | 7.1 |
| PCSb | 325 | 332 | 1.0 | 363 | 727 | 2.0 |
| PCSPb | 478 | N.D. | — | 462 | 1031 | 2.2 |

US 7,341,848 B2

ISOMALTOSE SYNTHASE-KNOCKOUT MICROORGANISM BELONGING EUMYCOTA

TECHNICAL FIELD

The present invention relates to a microorganism used for producing a protein. More particularly, the present invention relates to a microorganism that can be used as a host for preparing a microorganism for producing a protein, a microorganism for producing a protein, and a method for producing a protein by using the microorganism.

BACKGROUND ART

Filamentous fungi are known to secrete various enzyme proteins to the outside of the cell body. By using such a property of filamentous fungi, from old times, various filamentous fungi, in particular, filamentous fungi such as of the genus *Aspergillus*, have been widely used in brewing field for producing bean paste, soy sauce, sake, and the like, and in production of enzyme preparations. As a result of breeding for a long time for enhancing the production ability of extracellular enzyme, a strain capable of producing several tens grams of enzyme proteins per litter of a culture solution has been obtained.

On the other hand, with a recent application of a genetic recombination technology, various proteins can be produced. In the production of enzyme proteins using recombinant bacteria, as a means for producing a large amount of target enzymes, promoters having stronger transcription ability have been searched to be used from the viewpoint that enhancement of the transcription ability of genes may lead to high production. From such a viewpoint, hitherto, various promoters derived from filamentous fungi have been isolated and protein production systems using such promoters have been reported. For example, a promoter of the amylase gene of *Aspergillus oryzae* (see, for example, Japanese Patent Unexamined Publication No. S62-272988 and Biotechnology, 5,368 (1987)), a promoter of the glucoamylase gene of *Aspergillus nigar* (see, for example, Biotechnology, 6, 1419 (1988)), and the like, have been isolated and used. In addition, enhancement of the ability of promoters by introducing an enhancer or modifying a regulation region, and the like, has been carried out. According to the production of gene products depending upon the ability of promoters as mentioned above, the production ability has been more efficiently enhanced as compared with the enhancement of ability by a conventional breeding method. However, in order to increase an absolute amount of the production of extracellular enzyme proteins, further improvement in breeding of host strains by applying a conventional breeding method has been carried out.

DISCLOSURE OF INVENTION

In view of the above-mentioned background, an object of the present invention is to provide a host microorganism capable of efficiently enhancing an expression of a gene encoding a target protein when the gene is introduced. Another object of the present invention is to provide a transformant capable of producing a target protein with high efficiency. Further object of the present invention is to provide a production method capable of producing a target protein with high productivity.

In order to solve the above-mentioned problems, the present inventors have made various investigations while focusing Taka-amylase A of *Aspergillus*. The Taka-amylase A of *Aspergillus* is a typical inducible enzyme that is induced by starch or maltose and suppressed by glucose. The detail analysis of an inducing mechanism of Taka-amylase A of *Aspergillus* has revealed that the transcription induction is controlled by AmyR and real transcription inducing substance is isomaltose. It is revealed that the transcription induction of the Taka-amylase A gene of *Aspergillus* is caused by isomaltose generated as a result of α-glucosidase acting on starch or maltose.

The present inventors focused on α-glucosidase B that is a major isomaltose synthase in *Aspergillus nidulans* in the process for elucidating the induction mechanism of Taka-amylase A gene of *Aspergillus*, and produced a mutant strain (ΔagdB strain) lacking the same. Then, the present inventors introduced the Taka-amylase A gene into the mutant strain. In the thus obtained transformant, when the inducing effect of Taka-amylase A gene was examined by using starch and maltose as a source of isomaltose, it was found that the Taka-amylase A gene was expressed more strongly as compared with a control (a transformant in which the Taka-amylase A gene is introduced by using a wild type strain as a host). From these results, the following findings were obtained. That is, for the purpose of producing a protein encoding a gene that is induced to express by isomaltose, it is extremely effective to use a microorganism lacking a major isomaltose synthase gene as a host. The present invention was completed based on such a finding and provides the below mentioned configurations.

[1] A microorganism which belongs to *Eumycota* and lacks a major isomaltose synthase gene.

[2] The microorganism described in [1], which is classified in filamentous fungi.

[3] *Aspergillus nidulans* which lacks an α-glucosidase B gene.

[4] A transformant obtained by introducing a foreign gene whose expression is induced by isomaltose into a microorganism which belongs to *Eumycota* and lacks a major isomaltose synthase gene.

[5] The transformant described in [4], wherein the microorganism is classified in filamentous fungi.

[6] A transformant obtained by introducing a foreign gene whose expression is induced by isomaltose into *Aspergillus nidulans* which lacks an α-glucosidase B gene.

[7] The transformant described in any of [4] to [6], wherein the foreign gene contains the following modified promoter:
 a modified promoter obtained by inserting a first DNA fragment containing CCAATNNNNN (first base sequence: SEQ ID NO: 1) and a second DNA fragment CGGNNNNNNNNNGG (second base sequence: SEQ ID NO: 2) into a promoter capable of functioning in filamentous fungi.

[8] A method of producing proteins, the method comprising:
 a step of culturing the transformant of any of [4] to [7] under the conditions capable of allowing the foreign gene to express; and
 a step of collecting the produced proteins.

BRIEF DESCRIPTION OF DRAWINGS

FIG. 1 shows a sequence of a promoter region of the Taka-amylase A gene (*Aspergillus oryzae*).

FIG. 4 is a table summarizing measurement results of the amylase activity in Example 4. "N.D." in the table represents "Not Determined."

BEST MODE FOR CARRYING OUT THE INVENTION

Figure 2:
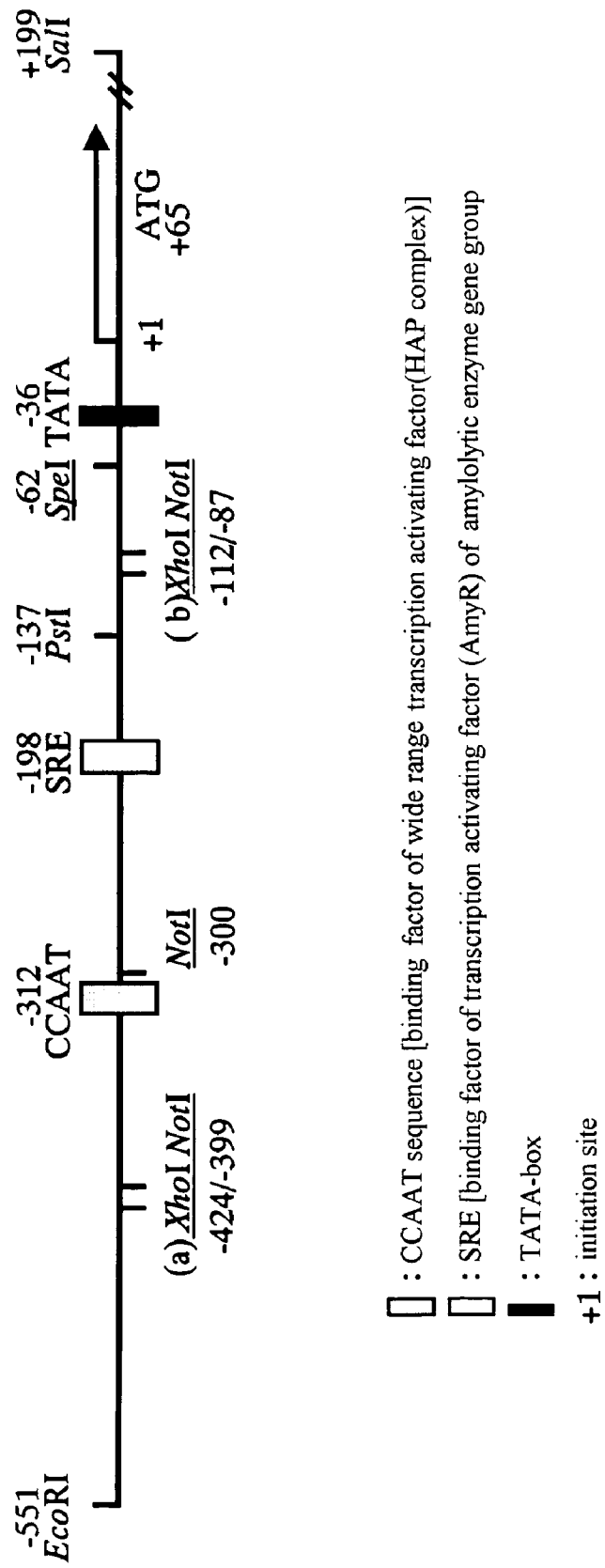
FIG. 2 is a schematic view of a promoter region of the Taka-amylase A gene (*Aspergillus oryzae*), which shows the position of the transcription controlling factor binding sequence (CCAAT sequence, SRE) and the portion in which a mutation is introduced. A restriction site introduced by a site-specific mutation is underlined. CCAAT denotes a CCAAT sequence (a binding factor of a wide range transcription activating factor (HAP complex)), SRE denotes a binding factor of a transcription activating factor (AmyR) of amylolytic enzyme gene group, TATA denotes a TATA-box, and +1 denotes a transcription start point, respectively.

Hereinafter, the present invention will be described in detail. A first aspect of the present invention is to provide a microorganism that belongs to *Eumycota* and lacks a major isomaltose synthase gene. The microorganism can be used as a host in the case of producing a transformant to be used for producing a certain protein. The "microorganism which belongs to *Eumycota*" of the present invention is not particularly limited. An example thereof includes filamentous fungi (including Chytridiomycota, Zygomycota, Ascomycota, Urediniomycetes and Deuteromycetes) such as *Aspergillus oryzae, Aspergillus nidulans, Aspergillus niger, Aspergillus awamori, Penicillium chrysogenum, Neurospora crassa, Trichoderma ressei*, and the like. Note here that "filamentous fungi" in the present invention broadly means filamentous fungi and includes also yeast (Ascomycota, Basidiomycotina, and Deuteromycetes)

The "major isomaltose synthase" of the present invention is an enzyme that is most involved in the production of isomaltose in the microorganism. That is to say, when the microorganism of interest has different kinds of enzymes having a production activity of isomaltose, the enzyme having the highest activity among the plurality of enzymes corresponds to the major isomaltose synthase herein. It is sufficient that the microorganism of the present invention lacks at least a gene encoding such an enzyme. For example, the microorganism may also lack an additional gene of another enzyme (which may be a plurality of enzymes when two or more enzymes exist) involving in the production of isomaltose. Specific examples of the isomaltose synthase may include α-glucosidase A, α-glucosidase B, transglucosidase, glucoamylase, and isopllulanase.

The microorganism of the present invention can be produced by selecting an appropriate microorganism from naturally existing microorganisms or microorganisms available from a storage agency, etc. and by submitting the selected microorganism to a mutation treatment so that it lacks a gene encoding the major isomaltose synthase. An example of the mutation treatment includes, for example, a method in which a vector including a gene obtained by providing a mutation to a gene to be lacked is prepared, and this is incorporated into a chromosome of a host microorganism by means of a genetic engineering technique, thereby destroying the target gene existing on a chromosome of the host microorganism; a site-specific mutation method, and the like.

A second aspect of the present invention relates to a transformant obtained by introducing a foreign gene into the above-mentioned host microorganism. Concretely, the present invention provides a transformant obtained by introducing a foreign gene whose expression is induced by isomaltose into a microorganism that belongs to *Eumycota* and lacks a major isomaltose synthase gene. Such a transformant of the present invention can be used for the production of proteins.

The transforming method used for producing the transformant of the present invention is not particularly limited and an appropriate method can be selected from the well-known methods. For example, it can be conducted by a method by Turner et al. using, for example, fungus body as a protoplast (see Gene, 36, 321-331 (1985)). Besides, a method by Gomi et al. (Agric. Biol. Chem., 51, 323-328 (1987)) may be employed.

When the transformation is carried out by using a vector, the kind of vectors to be used is not particularly limited. For example, it is possible to use a vector obtained by preparing a commercially available vector, which is suitable for transformation in relation to the host, and introducing a target gene into this prepared vector.

It is preferable that a selection marker, which is suitable for selecting the transformant when the transformation is carried out, is incorporated into a vector. The selection marker, which is suitable in relation to the host to be used, is employed. A specific example of the selection marker may include an auxotrophic complementary gene such as an ornithine carbamoyltransferase gene (argB), a nitrate reductase gene (niaD), an acetamidase gene (amdS), a tryptophan synthase gene (trpC), a dihydrofolate reductase gene (DHFR), etc., and drug resistance gene such as oligomycin, destomycin, hygromycin, etc., and the like.

The foreign gene used in the present invention includes a promoter and a structural gene (coding region) in principle. However, when a promoter of a host microorganism used for the transformation can be used (including a case where an appropriate promoter was introduced in a host microorganism in advance), as the foreign gene of the present invention, a gene without a promoter region, that is, a gene including only a coding region, a gene including only a coding region and a terminator, or the like, may be used.

As the promoter, one having a property of being inducible by isomaltose is used. Meanwhile, as the structural gene, one that is under control of the promoter after it is incorporated into a transformant is used. The promoter and the structural gene are not particularly limited as long as they satisfy the above-mentioned conditions. As a promoter, for example, a promoter capable of being induced by isomaltose in a gene encoding a protein in a microorganism belonging to, for example, the genus *Aspergillus, Penicillium, Trichoderma*, etc. can be used. More specifically, the promoter of gene encoding α-amylase, glucoamylase, α-glucosidase, etc. of the genus *Aspergillus* can be used. Among them, it is preferable to use a promoter of Taka-amylase of *Aspergillus oryzae*. Such a promoter can be obtained from a microorganism having it by a genetic engineering technique such as the restriction enzyme treatment, the PCR method, and the like. Furthermore, when a vector, in which the target promoter is incorporated, can be used, a promoter can be obtained from such a vector by the restriction enzyme treatment, the PCR method, and the like. On the other hand, as the structural gene, for example, a gene encoding a carbohydrate active enzyme such as α-amylase, glucoamylase, α-glucosidase, cellulose, pectinase, etc., a gene encoding a proteinase such as chymosin, a gene encoding lipase, or the like, can be used. Note here that a gene encoding a homologous protein or gene encoding a heterologous protein may be used. The homologous protein herein denotes a protein provided by a host microorganism in nature. On the other hand, the heterologous protein herein denotes a protein that is not produced by a host microorganism in nature, that is, a protein that can be produced only after a gene encoding it is introduced extraneously.

In transformation, the promoter and the structural gene (encoding region) are not required to be provided by the same vector. That is to say, a first vector having a promoter to be introduced and a second vector having a structural gene to be introduced are prepared and both are used for transformation, whereby a transformant in which a target foreign gene is introduced may be obtained.

A modified promoter obtained by modifying a naturally existing promoter can be used. Hereinafter, specific examples of the modified promoters are shown. Note here that in the following description, a function capable of enhancing the promoter activity is referred to as "an enhancer function."

(1) A modified promoter obtained by inserting a first DNA fragment containing CCAATNNNNNN (first base sequence: SEQ ID NO: 1) and a second DNA fragment containing CGGNNNNNNNNNGG (second base sequence: SEQ ID NO: 2) into a promoter capable of functioning in filamentous fungi.

(2) The modified promoter described in (1), wherein the first base sequence is CCAATTAGAAG (SEQ ID NO: 3).

(3) The modified promoter described in (1) or (2), wherein the second base sequence is CGGHNWWWWN-WHGG (SEQ ID NO: 4).

(4) The modified promoter described in (1) or (2), wherein the second base sequence is CGGWWWWWWW-WHGG (SEQ ID NO: 5).

(5) The modified promoter described in (1) or (2), wherein the second base sequence is CGGAAAATTTAAAGG (SEQ ID NO:6), CGGAATTTAAACGG (SEQ ID NO: 7) or CGGAAATTTAACGG (SEQ ID NO: 8).

(6) The modified promoter described in one of (1) to (5), wherein the first DNA fragment and the second DNA fragment are inserted in a way in which the first DNA fragment and the second DNA fragment are aligned in this order from the side of 5' terminal to the side of 3' terminal.

(7) The modified promoter described in (6), wherein the first DNA fragment and the second DNA fragment are inserted in an upstream region at the side of 5' terminal from a CCAAT sequence existing in the promoter or in a downstream region at the side of 3' terminal from a SRE region existing in the promoter region.

(8) The modified promoter described in any of (1) to (7), wherein a plurality of the first DNA fragments and a plurality of the second DNA fragments are inserted.

(9) The modified promoter described in (8), wherein the same number of the first DNA fragments and the second DNA fragments are inserted.

(10) The modified promoter described in (9), wherein the first DNA fragment and the second DNA fragment form a pair and the first DNA fragment and the second DNA fragment are inserted in the promoter so that the first DNA fragment is located at the side of 5' terminal in each pair.

(11) A modified promoter obtained by inserting one to several DNA fragments having base sequence of SEQ ID NO: 9 or DNA fragments a part of which are modified and which has an enhancer function into a promoter capable of functioning in filamentous fungi.

(12) The modified promoter described in any of (1) to (11), wherein the promoter capable of functioning in the filamentous fungi is a promoter of Taka-amylase of *Aspergillus oryzae*.

Note here that in the above, N denotes any of A, T, C and G.

The first DNA fragment and the second DNA fragment in the above-mentioned modified promoters can be synthesized by using, for example, a commercially available DNA synthesizer. Furthermore, they can also be prepared by the PCR method using an appropriate primer by using a promoter region of, for example, the Taka-amylase A gene of *Aspergillus oryzae* as a template.

The modified promoter can be produced by preparing a DNA fragment containing the first DNA fragment and the second DNA fragment and incorporating the thus prepared DNA fragment into a promoter functioning in filamentous fungi. Such a DNA fragment can be prepared by selecting a promoter including sequences corresponding to the first DNA fragment and the second DNA fragment from the promoters in, for example, the genera *Aspergillus*, and carrying out the PCR method using the selected promoter as a template. An example of a suitable promoter that can be used as a template may include a promoter (SEQ ID NO: 12) of the Taka-amylase A gene of *Aspergillus oryzae*. One example of the base sequence of the DNA fragment to be used for the modification of the promoter is shown in SEQ ID NO: 9. This DNA fragment (CCAAT-SRE fragment) is a part of the promoter region in the Taka-amylase A gene of *Aspergillus oryzae* (sequence from positions 240 to 367 (sequence from positions −312 to −185 when the initiation site is defined as +1)). Note here that even in a case where a part of this DNA fragment is modified, it can be used for the modification of a promoter region as long as it has a function for enhancing the activity of the promoter to be incorporated (enhancer function). Herein, modification of "a part of this DNA fragment is modified" is intended to include a case where a part of the base sequence constituting a DNA fragment is substituted or deleted, or a case where one to several bases are added or inserted. The level in which such a modification is accepted depends upon the site on the DNA fragment to be modified. Since a part that is important to the enhancer function is a part of the sequence corresponding to the first DNA fragment and the second DNA fragment, it is preferable that the level of the modification on the part is as small as possible. On the other hand, since it is expected that other parts are not involved in the enhancer function, relatively large modification is thought to be acceptable. For example, 1 to 20, preferably 1 to 10, and further preferably 1 to 5 bases can be substituted, deleted and added, etc. Note here that such a modification may include an introduction of a sequence cut by a restriction enzyme or addition of a sequence encoding a signal peptide, and the like, into 5' terminal and 3' terminal or other sites.

In the above-mentioned modified promoter, a modified promoter is constructed by inserting a first DNA fragment and a second DNA fragment (hereinafter, these DNA fragments and DNA fragment containing the same together will be referred to as "DNA fragment having an enhancer function") into a promoter capable of functioning in filamentous fungi. Herein, the insertion sites of these DNA fragments are not particularly limited. However, when a promoter having a CCAAT sequence and SRE is employed as a promoter to be modified, the insertion sites are preferably at the site other than the site between these two sequences. That it to say, it is preferable that a DNA fragment having an enhancer function is inserted in the site at 5' terminal side from the CCAAT sequence or the site at 3' terminal side from the SRE.

The modified promoter can be produced by inserting a plurality of the first DNA fragments and a plurality of the second DNA fragments into the promoter capable of functioning in filamentous fungi. In this case, it is preferable that the same number of the first DNA fragments and the second DNA fragments are used. Furthermore, it is preferable that one first DNA fragment and one second DNA fragment form a pair and the first DNA fragment and the second DNA fragment are inserted in the promoter so that the first DNA fragment is located at the side of 5' terminal in each pair.

Also in the case where the DNA fragment containing the first DNA fragment and the second DNA fragment is used, a promoter may be modified by inserting a plurality of the fragments. Also in this case, when a promoter having a CCAAT sequence and SRE is employed as a promoter to be modified, it is preferable that the insertion sites are preferably at the site other than the site between these two sequences.

The improvement of the promoter activity can be further expected by modifying a promoter by incorporating a plurality of DNA fragments having an enhancer function.

The kind of a promoter capable of functioning in filamentous fungi used for the production of a modified promoter is not particularly limited as long as it has a feature of functioning in filamentous fungi. A promoter of a gene encoding a protein in a microorganism of, for example, the genus Aspergillus, Penicillium, Trichoderma, etc. can be used. More specifically, a promoter of a gene encoding α-amylase, glucoamylase, α-glucosidase, etc. of the genus Aspergillus can be used. Among them, it is preferable to use a promoter of Taka-amylase of Aspergillus oryzae. Such promoters can be obtained from microorganisms having them by a genetic engineering technique such as the restriction enzyme treatment, the PCR method, and the like. Furthermore, when a vector, in which the target promoter is incorporated, can be used, a promoter can be obtained from such a vector by the restriction enzyme treatment, the PCR method, and the like.

A target protein can be produced by culturing the transformant of the present invention under conditions capable of expressing the introduced foreign genes. An appropriate culture medium can be used in accordance with the transformant to be used. For example, it is possible to use various kinds of commercially available media or medium which is composed by adding components such as arginine, uridine, etc. that are necessary for the growth and selection of a transformant and promoting of the expression of protein into one of the media.

The target proteins are collected from a culture solution in which the transformant was cultured for a predetermined time or a cell body. When proteins are of a secretion type, they are collected from a culture solution, and when proteins are of other type, they can be collected from a cell body. When proteins are collected from the culture solution, the target protein can be obtained by removing insoluble substances via filtration and centrifugation of the culture supernatant, followed by separating and purifying via the combination of salting-out such as ammonium sulfate precipitation, dialysis, various chromatographies, and the like. On the other hand, when proteins are collected from the cell body, for example, the target protein can be obtained by separating and purifying as mentioned above after the cell bodies are crushed by pressure treatment, ultrasonic treatment, etc. Note here that after the cell bodies are collected from the culture solution in advance by filtration, centrifugation, and the like, the above-mentioned series of steps (crush, separation, and purification of the cell body) may be carried out.

EXAMPLES

Hereinafter, the present invention will be described in more detail with reference to Examples, but the present invention is not necessarily limited thereto.

Example 1

Purification of α-glucosidase B (agdB) and Cloning of agdB Gene (1-1) Purification of α-glucosidase B and Enzymatic Characteristic Aspergillus nidulans ABPU1 (pyrG89, biA1, wA3, argB2, pyroA4: Mol. Gen. Genet. (1997) 253: 520-528, Motoyama, T., M. Fujisawa, N. Kojima, H. Horiuchi, A. Ohta and M. Takagi.) was inoculated so that the number of spores became $10^6$/ml on a minimum medium (2 L) containing 2% starch as a carbon source, and shake-cultured at 37° C. for 24 hours. Cell bodies were separated by suction filtration, frozen with liquid nitrogen, and then crushed into powder in the presence of liquid nitrogen. 5 ml of extraction buffer (0.2 M MES-KOH buffer (pH 5.5) containing 0.5% Triton X-100, 1 mM EDTA and 2 mM PMSF) per 1 g in wet weight of the cell bodies was added so as to allow the cell bodies to be suspended, followed by homogenization with polythoron. Centrifugation (16,000×g, at 4° C. for 30 minutes) was carried out and the resultant supernatant was used as a cell extract. From this cell extract, α-glucosidase B was purified as follows.

The cell extract was dialyzed in 20 mM MES-KOH buffer (pH 5.5) containing 1 mM EDTA and 0.5 mM PMSF, and then applied to DEAE-Tyopearl 650M column (2.5×10 cm) that had been equilibrated with 20 mM MES-KOH buffer (pH 5.5) in advance. Proteins adsorbed to this column were eluted with linear concentration gradient of 200 ml of 0-0.5 M NaCl. A major active fraction of α-glucosidase eluted with 0.1 M NaCl was collected and dialyzed in 20 mM MES-KOH buffer (pH 5.5) containing 1.5 M ammonium sulfate. This active fraction was allowed to adsorb to a Phenyl SepharoseCL-4B column (1×12 cm) that had been equilibrated in the same buffer, and eluted with linear concentration gradient of 40 ml of 1.5-0 M ammonium sulfate. Active fractions eluted with 0 M ammonium sulfate was collected and dialyzed in 20 mM HEPES-KOH buffer (pH 7.4), and then concentrated to 1 ml by Centriprep YM-10. This concentrated sample was applied to Resource Q column that had been equilibrated with the same buffer. Resource Q column chromatography was carried out by using AKTA explorer 10S system. Proteins adsorbed to this column were eluted with linear concentration gradient of 60 ml of 0-1 M NaCl. An active fraction that had been eluted at salt level of 0.3 M was dialyzed in 20 mM HEPES-KOH buffer (pH 7.4) so as to form a purified enzyme.

This purified enzyme was constituted by 74 kDa and 54 kDa subunits and had optimum pH of 5.5, and exhibited pH stability in pH 5.0 to pH 8.5 and temperature stability of 90% or more in the temperatures of up to 45° C. The enzyme activity of this purified enzyme was completely lost in conditions of pH 4.0 or less, pH 11.0 or more and temperatures 60° C. or more.

This enzyme has a transglycosylation activity of position-selectively forming α-1,6 glucoside binding in addition to a decomposing activity. This enzyme exhibited high hydrolysis activity with respect to maltooligosaccharide and the highest reactivity with respect to maltotriose, and the reactivity of this enzyme was lowered in maltotetraose and maltopentaose in this order, which suggested that this enzyme exhibited lower reactivity with respect to maltooligosaccharide with higher polymerization. Furthermore, this enzyme also exhibited a hydrolysis activity with respect to isomaltose, nigerose, koji-biose and α,α-trehalose. However, this enzyme hardly exhibited an activity with respect to p-nitrophenyl glucoside, saccharose and starch. Furthermore, with the transglycosylation activity of this enzyme, glucose and a plurality of transglycosylated products were synthesized from maltose. The major transglycosylated products included isomaltose and panose. Six hours after the reaction started, transglycosylated products were produced in an amount corresponding to about 50% of maltose that had been added as a substrate. 60% of the transglycosylated products was isomaltose. Furthermore, when koji-biose and nigerose were used as a substrate, isomaltose was produced; and when isomaltose was used as a substrate, isomaltotriose was produced.

(1-2) Cloning of α-glucosidase B Gene

The above-mentioned purified enzyme preparation was applied to SDS-PAGE so as to separate 74 kDa and 55 kDa subunits, which were transferred to a Sequi-Blot PVDF membrane. Bands corresponding to 74 kDa and 55 kDa subunits were cut out from the membrane, and N-terminal amino acid sequence was determined with the use of a protein sequencer, Applied Biosystems model 473A. The N-terminal amino acid sequences of the 74 kDa and 55 kDa subunits were SQAGVDPLDRPGNDYVKD and QSHRQLGAGRWRSAVRH, respectively. Furthermore, in order to determine the internal amino acid sequence of each of the 74 kDa and 55 kDa subunits, purified enzyme was applied to SDS-PAGE so as to separate both subunits each of which was electrically eluted from acrylamide. Each of the subunits was decomposed by lysylendopeptidase, and the resultant peptide was fractioned by 15% SDS-PAGE and transferred to PVDF membrane electrophoretically. The N-terminal amino acid sequence of each major band was determined by using a protein sequencer. The N-terminal amino acid sequences of the major peptide (30 kDa) derived from the 74 kDa subunit and the major peptide (15 kDa) derived from the 55 kDa subunit were THLPQNPHLYGLGE and DVSHWLGDNISDWLSYRLSI, respectively.

Based on the N-terminal and the internal amino acid sequences of the 74 kDa subunit, N-terminal primers N1 (5'-ARGCNGGNGTIGAYCCIYTNGA-3') and N2 (5'-YTNGAYMGICCNGGIAAYGA-3') as well as primers corresponding to the internal amino acid sequence, I1 (5'-CCRTANARRTGIGGRTTYTGNGG-3') and a primer I2 (5'-TGIGGRTTYTGNGGIARRTGNGT-3') were designed, and they were submitted to a PCR. The PCR was carried out by using *A. nidulans* chromosome DNA as a template and primers N1 and I1. By using a part of the PCR product and primers N2 and I2, a PCR was carried out again, and a DNA fragment of a part (440 bp) of the agdB gene was amplified. *A. nidulans* chromosome DNA was digested with HindIII, and the HindIII-digestd DNA fragment was fractioned in accordance with the sizes by agarose electrophoresis. 5-7 kb DNA fragment that hybridizes the above-mentioned 440 bp of DNA fragment was linked to pBluescript II KS+ (STRATAGENE) so as to transform *Escherichia coil*, JM109 (STRATAGENE). Then, a transformant strain that hybridizes 440 bp DNA fragment was obtained. This transformant strain had 5.6 kb HindIII DNA fragment containing the agdB gene. This plasmid was named pGBH6. The base sequence of the cloned DNA fragment was determined by the use of LI-COR model 4000 DNA sequencer by the method by Sanger, et al. The agdB gene is made of 3,055 bp containing three short introns of 57 to 72 bp and encodes 995 amino acid residues. The base sequence (SEQ ID NO: 27) of this gene was registered in DDBJ/EMBL/GenBank. The accession number is AB057788. Chemically determined N-terminal amino acid sequences of 74 kDa and 55 kDa subunits correspond to the estimated amino acid sequence at position 21 to 39 and amino acid sequence at position 515 to 531, respectively. Furthermore, the internal amino acid sequences of both subunits also correspond to the estimated amino acid sequences at position 167 to 187 and position 637 to 656, respectively. These results show that α-glucosidase B is synthesized as one polypeptide precursor and formed in a hetero dimer structure through processing. The amino acid sequence from the N-terminal to the 20th amino acid has a typical characteristic of a signal peptide, which suggests that this enzyme is a secretion enzyme.

Example 2

Production of Modified Promoter (2-1) Sub-Cloning of Promoter Region

The Taka-amylase A gene promoter region and the Taka-amylase A gene coding region were prepared by using pTG-taa [Mol. Gene. Genet., 254, 119-126 (1997)] containing the Taka-amylase A gene (taaG2) (3164 bp) [Gene, 84, 319-327 (1989)] of an *Aspergillus oryzae* JCM02239 strain as the starting material.

First of all, from pTG-taa, 750 bp of EcoRI-SalI fragment containing the Taka-amylase A (taaG2) promoter region was obtained. This fragment was inserted into the EcoRI-SalI site in the multi-cloning site of plasmid pKF18K (TOYOBO CO., LTD.) and thereby a plasmid pKF-taaP containing the Taka-amylase promoter was obtained. The operation of introducing mutation into the promoter region and the construction of the modified promoter region were carried out by using this plasmid.

(2-2) Obtaining of DNA Fragment Containing Transcription Control Factor Binding Sequence A fragment containing a previously reported binding factor of wide range transcription activating factor (HAP), a CCAAT sequence [Mol. Gen. Genet., 237, 251-260 (1993)] and a binding factor of a transcription activating factor (AmyR) of amylolytic enzyme gene groups, SRE [Mol. Gen. Genet., 262, 668-676 (1999)] was obtained as follows.

First of all, a DNA fragment containing the CCAAT sequence alone was obtained by synthesizing XNF (5'-CCGCTCGAGGCACCATCCAATTA-GAAGCGCGGCCGCTAAACTAT-3': SEQ ID NO: 13) as synthesized DNA added with a XhoI site and a NotI site at the 5' terminal side and 3' terminal side of the CCAAT sequence, and XNR (5'-ATAGTTTAGCGGCCGCGCT-TCTAATTGGATGGTGCCTCGAGCGG-3': SEQ ID NO: 14) as a complementary strand of this sequence; mixing complementary strands of these synthesized DNA; and heating the mixture at 98° C. for 10 minutes, cooling down to 30° C. for two hours, and then cooling down to 4° C. for annealing.

On the other hand, a DNA fragment containing the SRE alone was obtained by synthesizing SREf (5'-GACTAGTTAACCTAGGGGCGGAAATTTAACGGGATGTTAACTAGTC-3': SEQ ID NO: 15) as a synthesized DNA added with a SpeI site and a HincII site at the 5' terminal side and 3' terminal side of SRE, respectively, and SREr (5'-GACTAGTTAACATCCCGTTAAATTTCCGCCCCTAGGTTAACTAGTC-3': SEQ ID NO: 16) as a complementary strand of this sequence, and by carrying out the same method as mentioned above. Hereinafter, the DNA fragment including only the CCAAT sequence which was produced herein is referred to as "CCAAT fragment," and the DNA fragment which includes only the SRE is referred to as "SRE fragment," respectively.

Then, a DNA fragment containing a region from the CCAAT sequence to the SRE (SEQ ID NO: 9, referred to as "a CCAAT-SRE fragment," hereinafter) was obtained by using the following primers and pKF-taaP prepared in (2-1) as a template through carrying out 30 cycles of PCRs. One cycle includes at 94° C. for 30 seconds, 54° C. for 30 seconds and 72° C. for 90 seconds of reactions. Note here that two kinds of fragments, that is, a fragment including a PstI site (SEQ ID NO: 10, hereinafter, referred to as "CCAAT-SRE (PstI) fragment") and a fragment including an XhoI-NotI site (SEQ ID NO: 11, hereinafter, referred to as "CCAAT-SRE (XhoI-NotI) fragment") were produced.

```
Upstream primer added with PstI site
                                      (SEQ ID NO: 17)
CSPf: 5'-AAACTGCAGACCACCTCTAGGCATCGGACG-3'

Downstream primer added with PstI site
                                      (SEQ ID NO: 18)
CSPr: 5'-TTTCTGCAGTGTTGATTTGTGGTTGAGTGG-3'

Upstream primer added with XhoI site
                                      (SEQ ID NO: 19)
CSXf: 5'-CGGCTCGAGGCATCGGACGCACCATCC-3'

Downstream primer added with NotI site
                                      (SEQ ID NO: 20)
CSNr: 5'-ATAGTTTAGCGGCCGCCGACTGTGATTTGTGGTTGAGTGG-3'
```

(2-3) Construction of Plasmid Containing Modified Promoter

A mutation was introduced into the Taka-amylase A gene promoter region as follows. First of all, in order to introduce a restriction site for modifying a promoter region into pKF-taaP prepared in (2-1), a site-specific mutation was introduced into pKF-taaP by using the following primers and Mutan-Super Express Km Kit (TAKARA). Note here that a sequence of a wild type promoter (SEQ ID NO: 12) is shown in FIG. 1 and the position of the introduced restriction site is shown in FIG. 2.

A primer for introducing a NotI site into a downstream region (position 465 in the Taka-amylase promoter shown in SEQ ID NO: 12):
Not-b:

```
                                      (SEQ ID NO: 21)
5'-CGCTTGGATTCCCCGCCCGCGGCCGCAGAGCTTAAAGTATGTCCC-3'
```

A primer for introducing an XhoI site into a downstream region (position 440 in the Taka-amylase promoter shown in SEQ ID NO: 12):
Xho-b;

```
                                      (SEQ ID NO: 22)
5'-GAATGCAATTTAAACTCTTCCTCGAGTCGCTTGGATTCCCCGCCC-3'
```

A primer for introducing a NotI site into an upstream region (position 153 in the Taka-amylase promoter shown in SEQ ID NO: 12):
Not-a:

```
                                      (SEQ ID NO: 23)
5'-GTAGTAAAACCCCGGAGTCAGCGGCCGCCAAGCCCAAGTCCTTCACG-3'
```

A primer for introducing an XhoI site into an upstream region (position 128 in the Taka-amylase promoter shown in SEQ ID NO: 12):
Xho-a:

```
                                      (SEQ ID NO: 24)
5'-CGTCAAGGGATGCAAGACTCGAGTAGTAAAACCCCGGAGTC-3'
```

A primer for introducing a NotI site into a region sandwiched between the CCAAT sequence and SRE (the position 252 in the Taka-amylase promoter shown in SEQ ID NO: 12):
Not:

```
                                      (SEQ ID NO: 25)
5'-GCACCATCCAATTAGAAGCGCGGCCGCGAAACAGCCCAAGAAAAAGG-3'
```

A primer for introducing a SpeI site into a downstream region (position 490 in the Taka-amylase promoter shown in SEQ ID NO: 12):

```
                                      (SEQ ID NO: 26)
STATA: 5'-TAAAGTATGTCACTAGTCGATGCGAT-3'
```

Then, the CCAAT fragment prepared in (2-2) was cut with XhoI and NotI, submitted to agarose gel electrophoresis and then collected and purified. The resultant DNA fragment was inserted into an XhoI-NotI site that had been introduced into the downstream region of the promoter as mentioned above, whereby a plasmid pKF-CCAATb containing a modified promoter PCCAATb was produced. Similarly, a plasmid pKF-SREb containing a modified promoter PSREb in which a DNA fragment obtained by cutting the SRE fragment prepared in (2-2) with HincII was inserted into the XhoI-NotI site in the downstream region of the promoter; a plasmid pKF-PCSP containing a modified promoter PCSP in which a DNA fragment obtained by cutting the CCAAT-SRE (PstI) fragment prepared in (2-2) with PstI was inserted into a PstI site in the downstream region of the promoter; and a plasmid pKF-PCSb containing a modified promoter PCSb in which a DNA fragment obtained by cutting the CCAAT-SRE (XhoI-NotI) fragment prepared in (2-2) with XhoI and NotI was inserted into a XhoI-NotI site in a downstream region of the promoter were produced, respectively. Furthermore, the CCAAT-SRE (XhoI-NotI) fragment was cut with XhoI and NotI, and then the collected and purified fragments were inserted into an XhoI-NotI site of the downstream region of the promoter. Thereafter, by inserting the CCAAT-SRE (PstI) fragment into the PstI site, the plasmid pKF-PCSPb containing a modified promoter PCSPb in which the CCAAT-SRE fragment was inserted into two positions was prepared.

Example 3

Construction of Expression Vector of Amylase Gene

Figure 3:
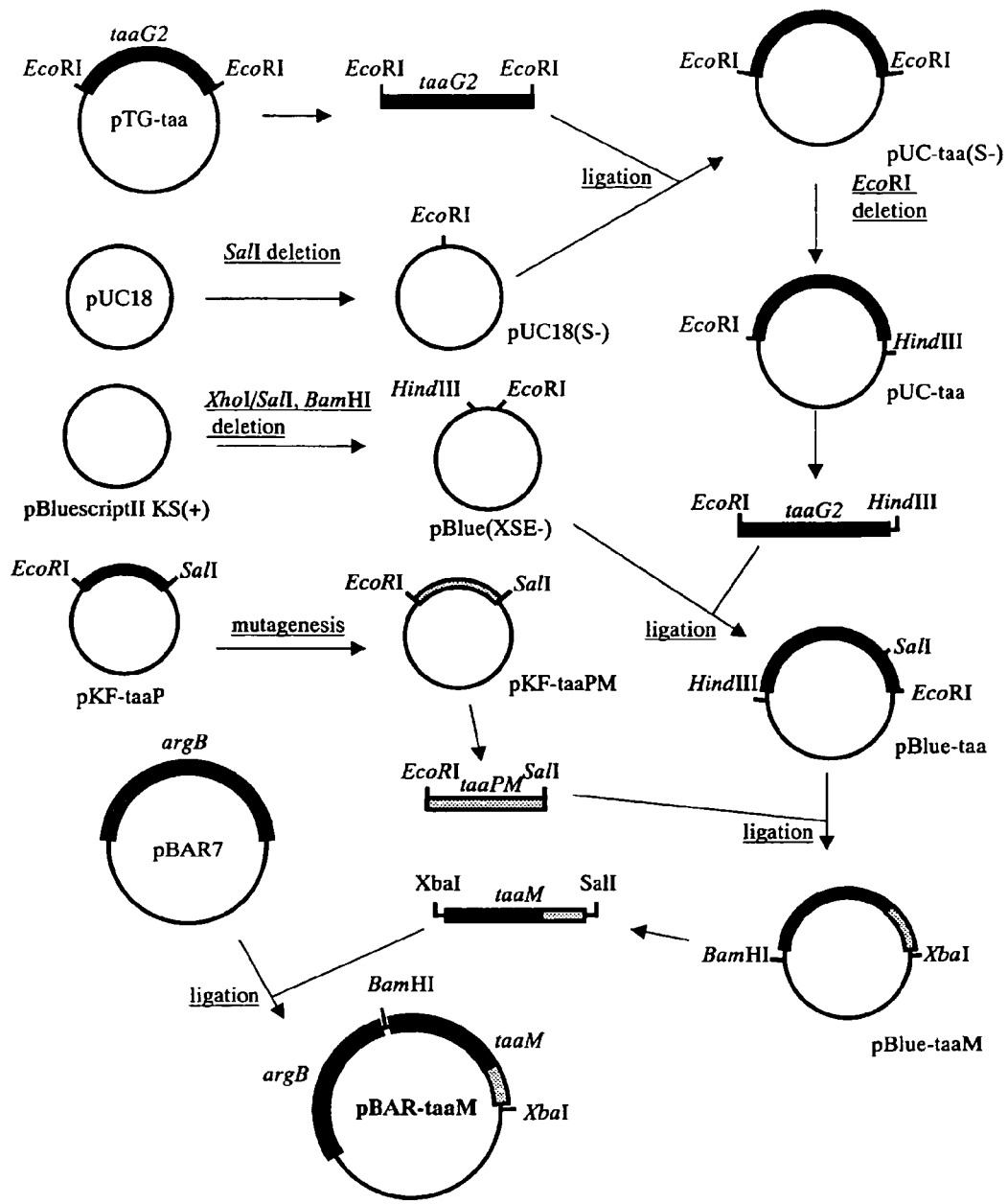
FIG. 3 shows a process for producing an amylase gene expression vector in Example 3.

FIG. 3 shows a process of producing an amylase gene expression vector. First of all, after plasmid pUC18 (TOYOBO CO., LTD.) was digested with SalI, blunted by a Klenow treatment, and self-ligated so as to obtain a plasmid pUC18 (S-) that lacks a SalI site. On the other hand, an EcoRI fragment of the Taka-amylase A gene was isolated from a plasmid pTG-taa. This fragment was inserted into the EcoRI site in the multi-cloning site of pUC18(S-) so as to obtain pUC-taa(S-). This plasmid, pUC-taa (S-), was partially decomposed with EcoRI so as to obtain a plasmid pUC-taa that lacks an EcoRI site at the 3' terminal side of the taaG2 gene. Similarly, a plasmid pBlue (XSE-) that lacks XhoI, SalI and BamHI of pBluescriptII KS (+) was obtained.

Then, an EcoRI-HindIII fragment containing taaG2 was isolated from pUC-taa, and this fragment was inserted into the EcoRI-HindIII site in the multi-cloning site of the plasmid pBlue (XSE-) so as to obtain a plasmid pBlue-taa containing taaG2.

Then, an EcoRI-SalI fragment of a modified promoter region was isolated from a plasmid pKF-taaPM series (pKF-CCAATb, pKF-SREb, pKF-PCSP, pKF-PCSb or pKF-PCSPb) containing the modified promoter obtained in (2-3) and inserted into the EcoRI-SalI in the multi-cloning site of a plasmid pBlue-taa so as to obtain a plasmid pBlue-taaM in which the modified promoter region and the taaG2 gene were connected to each other. An XbaI-BamHI fragment of the taaG2 gene containing a modified promoter was isolated from pBlue-taaM and incorporated into the XbaI-BamHI site in the multi-cloning site of a plasmid pBAR7 (a plasmid in which the argB gene that lacks C terminal derived from *Aspergillus nidulans* into pBluescriptII KS (+)) so as to obtain as a plasmid pBAR-taaM series (pBAR-CCAATb, pBAR-SREb, pBAR-PCSP, pBAR-PCSb and pBAR-PCSPb) for measuring the promoter activity. Note here that a plasmid having a wild type promoter was produced by the similar procedure and this was defined as pBAR-taa.

Example 4

Obtaining of Transformant Having Strain that Lacks α-glucosidase B as Host (4-1) Construction of α-glucosidase B (agdB) Gene Disruption Strain pGBS5 was constructed by sub-cloning a part (4.9 kb) of a SacI fragment (−3,132 to +1,689) of the agdB gene contained in the plasmid pGBH6 obtained in (1-2) to pBluescriptII KS(+). pGBA8 was constructed by linking ClaI-HindIII 4.9 kb fragment (+222 to +4,726) of pGBH6 and ApaI-ClaI 3.1 kb fragment (−2,834 to +221) that had been prepared from pGBS5 to pBluescript IIKS+ that had been digested with ApaI and ClaI. A plasmid pGBΔP2 for destroying the agdB gene was constructed by substituting a SalI1 fragment (corresponding to −181 to +3,435 of the agdB gene) by a BspI 2.0 kb fragment containing the *N. crassa* pyr4 gene. Note here that BspI 2.0 kb fragment was prepared from pTG1 (Mol. Gen. Genet. (1997) 254: 119-126, M. Kato, A. Aoyama, F. Naruse, T. Kobayashi, and N. Tsukagoshi) containing the pyr4 gene. Then, 5.9 kb KpnI-SpeI fragment containing the agdB gene destroyed from pGBΔP2 was prepared, and *A. nidulans* ABPU1 was transformed so as to obtain ΔagdB strain DBP9. The insertion of the pry4 gene into the agdB site was confirmed by Southern blotting analysis. Note here that this strain is deposited with the following depositary agency.

Accession number: FERM P-19070
Depositary agency: National Institute of Advanced Industrial Science and Technology, International Patent Organism Depositary
Chuo No. 6, 1-3, Higashi 1-chome, Tsukuba-shi, Ibaraki-ken, 305-8566, Japan
Deposition date: Oct. 18, 2002

(4-2) Transformation

Transformation of filamentous fungi was carried out as follows. First of all, after each of the plasmids pBAR-taa, pBAR-PCSb and pBAR-PCSPb was digested with EcoRV, operations of phenol/chloroform extraction and ethanol precipitation were carried out and purified plasmid was used for transformation. The transformation was carried out as follows. A strain DBP9 ((pyrG89) biA1 wA3 argB2pyroA4 ΔagdB::pyr4) lacking α-glucosidase of *Aspergillus nidulans* obtained in (4-1) and an *Aspergillus nidulans* ABPU1 strain (biA1 pyrG89 wA3 argB2 pyroA4) as a control strain were shake-cutured over night at 37° C. in a medium obtained by adding necessary nutrients (arginine, uridine, pyridoxine and biotin) to a complete medium (2% malt extracts, 2% glucose and 0.1% bactopeptone). Then, the obtained cell bodies were suspended in a cell wall lytic solution [20 mg/ml Yatalase (Takara Shuzo Co., Ltd.) and 0.8 M NaCl and 10 mM phosphate buffer solution (pH6.0)] and shaken gently at 30° C. for 1 to 2 hours so as to obtain protoplasts. The obtained protoplasts were filtrated through a nylon filter, thereby removing the remaining cell bodies. Then, by using these protoplasts and each of the purified plasmids, transformation was carried out by a method by Turner et al. [Gene, 36, 321-331 (1985)]. Consequently, 20 to 40 strains of transformant capable of growing in a medium without containing arginine (Czapek-Dox agar (0.2% $NaNO_3$, 0.1% $K_2HPO_4$, 0.05% KCl, 0.05% $MgSO_4$-$7H_2O$ and 2% glucose (pH5.5)) were obtained per each plasmid.

(4-3) Selection of Transformant by Southern Blotting Analysis

A genomic DNA was prepared from each transformant strain as follows. First of all, a transformant strain was shake-cultured over night at 37° C. in a medium obtained by adding necessary nutrients (uridine, pyridoxine and biotin) to a complete medium, then the obtained cell bodies were collected with a Buchner funnel and filter paper No.2 (Advantech) and washed in sterile water. Extra water was removed, followed by freezing it at −80° C. and drying it with the use of FREEZONE (LABCONCO). After drying, 1 mm of glass balls were added so as to crush the cell bodies into fine powders by using Multibeads Shocker (Yasui Kikai Corporation) at 2000 rpm for 5 minutes. To the crushed cell bodies, an extract solution [1% hexadecylmethylammoniumbromide, 0.7 M NaCl, 50 mM Tris-HCl, 10 mM EDTA and 1% β-mercaptoethanol] was added, stirred and allowed to stand for 30 minutes at room temperature. The obtained lysate was phenol/chloroform extracted so as to remove contaminating proteins, followed by adding an equal amount of isopropanol so as to precipitate DNA. These precipitates were dissolved in a TE solution containing 0.1 mg/ml RNase to effect a reaction at 37° C. for 30 minutes. Furthermore, a TE solution containing 0.2 mg/ml proteinaseK was added to effect a reaction at 37° C. for 30 minutes. This solution was phenol/chloroform extracted and allowed to precipitate in 2.5-fold volume of cold ethanol. These precipitates were rinsed with 70% ethanol, dried and then dissolved in a TE solution. The resultant solution was defined as a genomic DNA solution.

In Southern blotting analysis, genomic DNA was digested with PvuII or EcoRV, followed by separation by agarose gel electrophoresis so as to blot on nylon membrane (Roche Japan). Then, about 1000 bp of BglII-SmaI digested product of taaG2 was detected as a probe. At this time, labeling of probes and detection of signals were carried out by using DIG nucleic acid detection kit (Roche Japan).

From the results of Southern blotting analysis, a transformant strain suitable for comparison of the amylase producing ability of strains used as a host, that is, a transformant strain in which one pair of plasmids were complimentarily incorporated into an argB locus and which is capable of comparing the amylase producing ability without being affected by the position to be incorporated in the chromosome and by the number of copies of genes to be introduced was selected arbitrarily. Herein, two or more transformant strains per plasmid used were selected.

Example 5

Comparison of Amylase Activities

By using each of the transformants obtained in Example 4 into which pBAR-taa, pBAR-PCSb and pBAR-PCSPb were respectively incorporated, the amylase producing ability was compared by the following procedure between in the case where a strain lacking α-glucosidase B was used as a host and in the case where a strain lacking an ABPU1 strain was used as a host.

Firstly, each transformant was plated radially on an agar medium obtained by adding necessary nutrients (uridine, pyridoxine and biotin) to a minimum medium (0.9% $NaNO_3$, 0.05% KCl, 0.15% $KH_2PO_4$, 0.15% Trace element, 0.05% $MgSO_4$-$7H_2O$, and 1% glucose (pH6.5)) and cultured at 37° C. for three days. Thereafter, from this agar medium, conidiospores were suspended in a solution for suspending spores (0.01% tween80 and 0.8% NaCl) and filtrated with cotton so as to prepare a spore solution. $1\times10^8$ conidiospores from this spore solution were inoculated on a medium obtained by adding necessary nutrients other than arginine (uridine, pyridoxine and biotin) to an SP medium (1% Starch, 1% polypeptone, 0.5% $KH_2PO_4$, 0.1% $NaNO_3$ and 0.05% $MgSO_4$-$7H_2O$ (pH6.5)) or an MP medium (1% Maltose, 1% polypeptone, 0.5% $KH_2PO_4$, 0.1% $NaNO_3$, and 0.05% $MgSO_4$-$7H_2O$ (pH6.5)), and shake-cultured at 37° C. for 36 hours, followed by separating cell bodies from supernatants with a Buchner funnel and filter paper. The supernatant was used as an enzyme solution.

The amylase activity was measured by preparing 150 µl of reaction system by adding the enzyme solution to 20 mM sodium acetate buffer, 10 mM $CaCl_2$ and 2% Soluble Starch (nachalai tesque); reacting them at 37° C. for 20 minutes to produce reduction sugar; and quantifying the amount of the thus produced reduction sugar by a Nelson-Somogyi method. Furthermore, an amount of enzyme allowing glucose to release at 1 µmol/minute was defied as 1 unit. Then, an amount of produced amylase from the measured value of the amylase activity was calculated and the amylase producing ability was compared by the following procedure between in the case where a strain lacking α-glucosidase B was used as a host and in the case where a strain lacking an ABPU1 strain was used as host.

The measurement results of the amylase activity are shown in FIG. 4. The production amount of amylase when the transformant of the taaG2 gene using a ΔagdB strain as a host was cultured in a medium containing starch as a C source was about six times as that using an ABPU1 strain as a host. This is thought to be because the decomposition of isomaltose that is an inducer is suppressed due to the lack of α-glucosidase B and the inducing effect is continued. From this result, it was confirmed that the lack of α-glucosidase B was very effective in enhancing the amylase producing ability.

Next, the amylase activity under the condition where culturing was carried out on the MP medium using maltose as a C source was measured. The production amount of amylase in the case of using a transformant of the taaG2 gene using the ΔagdB strain as a host was about seven times as that using the ABPU1 strain as a host. The production amount of amylase by a strain in which a modified promoter (PCSb or PCSPb) was incorporated using a ΔagdB strain as a host was about two times as that using the ABPU1 strain as a host. These results showed that when the C source such as maltose that synthesizes isomaltose easily was used for a medium, the use of a host that lacks the agdB gene could further enhance the amylase producing ability. Furthermore, it was revealed that the use of a modified promoter could provide higher productivity. Note here that as shown in FIG. 4, the maximum production amount of amylase obtained in the system of this Example was about 1 g/L.

The present application is accomplishment of "Basic study of process technology of environmentally compatible industry using high enzyme producing ability by mold" (2002) conducted as the commission study with research funding for promoting science and technology of Ministry Of Education, Science And Technology.

INDUSTRIAL APPLICABILITY

The present invention provides a host microorganism capable of efficiently enhancing the expression of a gene when the gene is extraneously introduced. When a transformant obtained by introducing a gene encoding a target protein into the host microorganism is used, the target protein can be produced with high productivity.

The invention claimed is:

1. A transformant obtained by introducing a foreign gene into a microorganism which belongs to *Aspergillus* which lacks an α-glucosidase B gene, wherein the foreign gene comprises a structural gene and a promoter promoting a transription of the structural gene, the promoter is a promoter whose transcription activity is induced by isomaltose, and the promoter is a promoter of α-amylase gene, glucoamylase gene, or α-gloucosidase gene of *Aspergillus*.

2. A transformant obtained by introducing a foreign gene into *Aspergillus nidulans* which lacks an α-glucosidase B gene, wherein the foreign gene comprises a structural gene and a promoter promoting a transcription of the structural gene, the promoter is a promoter whose transcription activity is induced by isomaltose, and the promoter is a promoter of α-amylase gene, glucoamylase gene, or α-glucosidase gene of *Aspergillus*.

3. A transformant obtained by introducing a foreign gene into a microorganism which belongs to *Aspergillus* which lacks an α-glucosidase B gene, wherein the foreign gene comprises a structural gene and a modified promoter obtained by inserting a first DNA fragment containing CCAATNNNNNN (first base sequence: SEQ ID NO: 1) and a second DNA fragment CGGNNNNNNNNNGG (second base sequence: SEQ ID NO: 2) into a promoter capable of functioning in *Aspergillus*, said modified promoter is a promoter whose transcription activity is induced by isomaltose.

4. A method of producing proteins, the method comprising:
  a step of culturing the transformant according to claim 1 under the conditions capable of allowing the foreign gene to express; and
  a step of collecting the produced proteins.

* * * * *

SEQUENCE LISTING

<160> NUMBER OF SEQ ID NOS: 27

<210> SEQ ID NO 1
<211> LENGTH: 11

```
<212> TYPE: DNA
<213> ORGANISM: Artificial Sequence
<220> FEATURE:
<223> OTHER INFORMATION: Description of Artificial Sequence: an enhancer
      sequence
<220> FEATURE:
<221> NAME/KEY: misc_feature
<222> LOCATION: (6)..(11)
<223> OTHER INFORMATION: n stands for any base

<400> SEQUENCE: 1
ccaatnnnnn n                                                            11

<210> SEQ ID NO 2
<211> LENGTH: 14
<212> TYPE: DNA
<213> ORGANISM: Artificial Sequence
<220> FEATURE:
<223> OTHER INFORMATION: Description of Artificial Sequence: an enhancer
      sequence
<220> FEATURE:
<221> NAME/KEY: misc_feature
<222> LOCATION: (4)..(12)
<223> OTHER INFORMATION: n stands for any base

<400> SEQUENCE: 2
cggnnnnnnn nngg                                                         14

<210> SEQ ID NO 3
<211> LENGTH: 11
<212> TYPE: DNA
<213> ORGANISM: Artificial Sequence
<220> FEATURE:
<223> OTHER INFORMATION: Description of Artificial Sequence: an enhancer
      sequence

<400> SEQUENCE: 3
ccaattagaa g                                                            11

<210> SEQ ID NO 4
<211> LENGTH: 14
<212> TYPE: DNA
<213> ORGANISM: Artificial Sequence
<220> FEATURE:
<223> OTHER INFORMATION: Description of Artificial Sequence: an enhancer
      sequence
<220> FEATURE:
<221> NAME/KEY: misc_feature
<222> LOCATION: (5)..(5)
<223> OTHER INFORMATION: n stands for any base
<220> FEATURE:
<221> NAME/KEY: misc_feature
<222> LOCATION: (10)..(10)
<223> OTHER INFORMATION: n stands for any base

<400> SEQUENCE: 4
cgghnwwwwn whgg                                                         14

<210> SEQ ID NO 5
<211> LENGTH: 14
<212> TYPE: DNA
<213> ORGANISM: Artificial Sequence
<220> FEATURE:
<223> OTHER INFORMATION: Description of Artificial Sequence: an enhancer
      sequence

<400> SEQUENCE: 5
cggwwwwwww whgg                                                         14
```

```
<210> SEQ ID NO 6
<211> LENGTH: 14
<212> TYPE: DNA
<213> ORGANISM: Artificial Sequence
<220> FEATURE:
<223> OTHER INFORMATION: Description of Artificial Sequence: an enhancer
      sequence

<400> SEQUENCE: 6
cggaaattta aagg                                                         14

<210> SEQ ID NO 7
<211> LENGTH: 14
<212> TYPE: DNA
<213> ORGANISM: Artificial Sequence
<220> FEATURE:
<223> OTHER INFORMATION: Description of Artificial Sequence: an enhancer
      sequence

<400> SEQUENCE: 7
cggaatttaa acgg                                                         14

<210> SEQ ID NO 8
<211> LENGTH: 14
<212> TYPE: DNA
<213> ORGANISM: Artificial Sequence
<220> FEATURE:
<223> OTHER INFORMATION: Description of Artificial Sequence: an enhancer
      sequence

<400> SEQUENCE: 8
cggaaattta acgg                                                         14

<210> SEQ ID NO 9
<211> LENGTH: 128
<212> TYPE: DNA
<213> ORGANISM: Artificial Sequence
<220> FEATURE:
<223> OTHER INFORMATION: Description of Artificial Sequence:a DNA
      fragment including CCAAT sequence and SRE

<400> SEQUENCE: 9
ccaattagaa gcagcaaagc gaaacagccc aagaaaaagg tcggcccgtc ggccttttct       60
gcaacgctga tcacgggcag cgatccaacc aacaccctcc agagtgacta ggggcggaaa      120
tttaaagg                                                              128

<210> SEQ ID NO 10
<211> LENGTH: 196
<212> TYPE: DNA
<213> ORGANISM: Artificial Sequence
<220> FEATURE:
<223> OTHER INFORMATION: Description of Artificial Sequence:a DNA
      fragment including CCAAT
      sequence and SRE

<400> SEQUENCE: 10
ctgcagacca cctctaggca tcggacgcac catccaatta gaagcagcaa agcgaaacag       60
cccaagaaaa aggtcggccc gtcggccttt tctgcaacgc tgatcacggg cagcgatcca      120
accaacaccc tccagagtga ctaggggcgg aaatttaaag ggattaattt ccactcaacc      180
acaaatcaca ctgcag                                                     196

<210> SEQ ID NO 11
<211> LENGTH: 193
<212> TYPE: DNA
```

<213> ORGANISM: Artificial Sequence
<220> FEATURE:
<223> OTHER INFORMATION: Description of Artificial Sequence:a DNA
      fragment including CCAAT
      sequence and SRE

<400> SEQUENCE: 11
ctcgagaggc atcggacgca ccatccaatt agaagcagca aagcgaaaca gcccaagaaa    60
aaggtcggcc cgtcggcctt ttctgcaacg ctgatcacgg gcagcgatcc aaccaacacc   120
ctccagagtg actaggggcg gaaatttaaa gggattaatt ccactcaac cacaaatcac    180 agtcggcggc cgc                                                      193

<210> SEQ ID NO 12
<211> LENGTH: 615
<212> TYPE: DNA
<213> ORGANISM: Aspergillus oryzae
<220> FEATURE:
<221> NAME/KEY: promoter
<222> LOCATION: (1)..(615)
<223> OTHER INFORMATION:

<400> SEQUENCE: 12
gaattcatgg tgttttgatc attttaaatt tttatatggc gggtggtggg caactcgctt    60
ccgggcaact cgcttaccga ttacgttagg gctgatattt acgtaaaaat cgtcaaggga   120
tgcaagacca aagtagtaaa accccggagt caacagcatc caagcccaag tccttcacgg   180
agaaacccca gcgtccacat cacgagcgaa ggaccacctc taggcatcgg acgcaccatc   240
caattagaag cagcaaagcg aaacagccca agaaaaggt cggcccgtcg gccttttctg    300
caacgctgat cacgggcagc gatccaacca acaccctcca gagtgactag ggcggaaat   360 ttaaagggat taatttccac tcaaccacaa atcacagtcg tccccggtat tgtcctgcag   420
aatgcaattt aaactcttct gcgaatcgct tggattcccc gccctggcc gtagagctta   480 aagtatgtcc cttgtcgatg cgatgtatca caacatataa atactagcaa gggatgccat   540
gcttggagga tagcaaccga caacatcaca tcaagctctc ccttctctga caataaaacc   600
ccacagaagg cattt                                                   615

<210> SEQ ID NO 13
<211> LENGTH: 44
<212> TYPE: DNA
<213> ORGANISM: Artificial Sequence
<220> FEATURE:
<223> OTHER INFORMATION: Description of Artificial Sequence: a PCR
      primer designed for amplifying CCAAT sequence

<400> SEQUENCE: 13
ccgctcgagg caccatccaa ttagaagcgc ggccgctaaa ctat                     44

<210> SEQ ID NO 14
<211> LENGTH: 44
<212> TYPE: DNA
<213> ORGANISM: Artificial Sequence
<220> FEATURE:
<223> OTHER INFORMATION: Description of Artificial Sequence: a PCR
      primer designed for amplifying CCAAT sequence

<400> SEQUENCE: 14
atagtttagc ggccgcgctt ctaattggat ggtgcctcga gcgg                     44

<210> SEQ ID NO 15
<211> LENGTH: 46

```
<212> TYPE: DNA
<213> ORGANISM: Artificial Sequence
<220> FEATURE:
<223> OTHER INFORMATION: Description of Artificial Sequence: a PCR
      primer designed for amplifying SRE

<400> SEQUENCE: 15
gactagttaa cctagggggcg gaaatttaac gggatgttaa ctagtc                46

<210> SEQ ID NO 16
<211> LENGTH: 46
<212> TYPE: DNA
<213> ORGANISM: Artificial Sequence
<220> FEATURE:
<223> OTHER INFORMATION: Description of Artificial Sequence: a PCR
      primer designed for amplifying SRE

<400> SEQUENCE: 16
gactagttaa catcccgtta aatttccgcc cctaggttaa ctagtc                46

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: a PCR
      primer designed for amplifying a DNA fragment including CCAAT
      sequence and SRE

<400> SEQUENCE: 17
aaactgcaga ccacctctag gcatcggacg                                   30

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: a PCR
      primer designed for amplifying a DNA fragment including CCAAT
      sequence and SRE

<400> SEQUENCE: 18
tttctgcagt gttgatttgt ggttgagtgg                                   30

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: a PCR
      primer designed for amplifying a DNA fragment including CCAAT
      sequence and SRE

<400> SEQUENCE: 19
cggctcgagg catcggacgc accatcc                                      27

<210> SEQ ID NO 20
<211> LENGTH: 40
<212> TYPE: DNA
<213> ORGANISM: Artificial Sequence
<220> FEATURE:
<223> OTHER INFORMATION: Description of Artificial Sequence: a PCR
      primer designed for amplifying a DNA fragment including CCAAT
      sequence and SRE

<400> SEQUENCE: 20
atagtttagc ggccgccgac tgtgatttgt ggttgagtgg                        40
```

<210> SEQ ID NO 21
<211> LENGTH: 45
<212> TYPE: DNA
<213> ORGANISM: Artificial Sequence
<220> FEATURE:
<223> OTHER INFORMATION: Description of Artificial Sequence:a primer for
     site-directed mutagenesis

<400> SEQUENCE: 21
cgcttggatt ccccgcccgc ggccgcagag cttaaagtat gtccc            45

<210> SEQ ID NO 22
<211> LENGTH: 45
<212> TYPE: DNA
<213> ORGANISM: Artificial Sequence
<220> FEATURE:
<223> OTHER INFORMATION: Description of Artificial Sequence:a primer for
     site-directed mutagenesis

<400> SEQUENCE: 22
gaatgcaatt taaactcttc ctcgagtcgc ttggattccc cgccc             45

<210> SEQ ID NO 23
<211> LENGTH: 47
<212> TYPE: DNA
<213> ORGANISM: Artificial Sequence
<220> FEATURE:
<223> OTHER INFORMATION: Description of Artificial Sequence:a primer for
     site-directed mutagenesis

<400> SEQUENCE: 23
gtagtaaaac cccggagtca gcggccgcca agcccaagtc cttcacg           47

<210> SEQ ID NO 24
<211> LENGTH: 41
<212> TYPE: DNA
<213> ORGANISM: Artificial Sequence
<220> FEATURE:
<223> OTHER INFORMATION: Description of Artificial Sequence:a primer for
     site-directed mutagenesis

<400> SEQUENCE: 24
cgtcaaggga tgcaagactc gagtagtaaa accccggagt c                 41

<210> SEQ ID NO 25
<211> LENGTH: 47
<212> TYPE: DNA
<213> ORGANISM: Artificial Sequence
<220> FEATURE:
<223> OTHER INFORMATION: Description of Artificial Sequence:a primer for
     site-directed mutagenesis

<400> SEQUENCE: 25
gcaccatcca attagaagcg cggccgcgaa acagcccaag aaaaagg           47

<210> SEQ ID NO 26
<211> LENGTH: 26
<212> TYPE: DNA
<213> ORGANISM: Artificial Sequence
<220> FEATURE:
<223> OTHER INFORMATION: Description of Artificial Sequence:a primer for
     site-directed mutagenesis

<400> SEQUENCE: 26
taaagtatgt cactagtcga tgcgat                                  26

<210> SEQ ID NO 27
<211> LENGTH: 5640
<212> TYPE: DNA
<213> ORGANISM: Aspergillus nidulans

<400> SEQUENCE: 27

| | | | | | | |
|---|---|---|---|---|---|---|
| aagcttgttg | aagccgtcaa | tccgcagcct | atctggttga | gttcgccggt | caaccgtact | 60 |
| gaaagtagca | ttgaggggca | gaacttattc | gtttcgagac | agcaatgaat | tctcaagtga | 120 |
| cacctatatc | tgcccagctg | ttgtctcttc | attcttcttt | ggaccaagtt | tttactggag | 180 |
| tacaatgacc | ctgtaatcct | accgggtggg | cctgatctgg | ccgtcggaga | acgtagggtt | 240 |
| tccctactgc | cctactgccc | tttactaggc | cattatcctg | tccaccacct | ttcgcttccg | 300 |
| gcttttcttt | ctttcatact | ttgctttcct | ccttgaaatt | gtttacttct | accattgtct | 360 |
| atcagtttct | tgttaagcca | cctctggtct | cccgggtggg | tatgggccga | tcccaatttc | 420 |
| gcagtcttgg | cacttttact | cgaagatgag | ggaaggtcaa | tcaggctcag | cctcattgag | 480 |
| cgataggccg | ccaattctca | acctagcgag | tacgagctta | agcagtttgg | cggagcccct | 540 |
| gttctagaag | ctgtccagct | cggtgtcctg | tatcatgaag | cgcattcgat | cgcttggctg | 600 |
| gcgtcagggt | tcgtccaacg | gcactgaatc | cacgatcact | actgggtaaa | caccccgcaa | 660 |
| gcgcctgggc | agcgaccaag | gtacggaagg | tccgggcttt | caaaaattac | cgcgggacta | 720 |
| ctccggagtc | gaccgttaag | cagggtcgat | gattgggtag | tgctggcgaa | gcgttgcatt | 780 |
| tgctcgggct | tttaccggag | actgcggagt | ccccaattct | tggcagtcca | tgaagcggag | 840 |
| tataaaaggc | gtccggcaag | aagatagagt | atcctgtaga | ccagctcttc | ctcactttgt | 900 |
| ggagtcaaga | tgcgctttca | gcagctgctt | ccatgggctg | cggccctgac | tggctgcgtc | 960 |
| gtcgcccaga | gccaggccgg | cgtcgatccg | ctcgaccgtc | ccggcaatga | cctctacgta | 1020 |
| aaggaccttt | cgaactgcac | tgggtacaag | gtcaccaagc | attggaagac | ccgatccggt | 1080 |
| ttctatgcgg | acctggcgct | cgccgggcca | gcatgcaatg | tgtacggaat | cgatttgccc | 1140 |
| aagctgaagc | tcgaagtcga | gtatcagacc | gatgagcgac | tgcacgtcaa | gattctggat | 1200 |
| accaacaaca | cagtttacca | ggtgccagac | agcgtcttcc | cgcgcccggg | cttcggccag | 1260 |
| tggtgctcgc | ccaagaactc | taagctcaag | tttgacttca | aacctgaccc | gttctcgttc | 1320 |
| accgtctctc | gcacagacac | cggcgaggtg | ctcttcgaca | ccaccggcac | caagctcgtg | 1380 |
| ttcgagaacc | agtatcttta | tctgaagacg | cacctgccgc | agaacccgca | tctgtatggt | 1440 |
| ctgggagagc | atagcgactc | cttcatgctc | aacaccacca | actacacccg | aacaatctac | 1500 |
| acccgtgatg | cttacgggac | gccccaaggc | cagaatctgt | acggggctca | cccgatctat | 1560 |
| ttcgatcacc | ggcaggacgg | cactcacggt | gtgttcctgc | tcaactccaa | cggtatggac | 1620 |
| atctacatcg | acaacgaggg | cggccagttc | ctcgagtaca | acatcatcgg | cggcgttttc | 1680 |
| gacttctact | tcatcgccgg | accatccccg | caagatgtgg | ccaggcagta | tgctgaaatt | 1740 |
| gtccagccgc | ccctgatggt | tccatactgg | ggactcggtt | tccaccagtg | caggtacggc | 1800 |
| taccaggatg | tctacgaggt | ggccgctgtc | accgccaact | actccgtcca | cgatatccca | 1860 |
| ctggagacca | tctggactga | tatcgactac | atggaccgtc | ggcgcatctt | cacgctcgat | 1920 |
| cccgaacgat | tcccaccaga | gctggtcaaa | gaccttgtgg | acactcttca | cgcgcgagat | 1980 |
| cagcattaca | ttgtcatggt | tgatccggct | gtctactaca | gcgagccaaa | cccggcgctt | 2040 |
| gacgccggtc | tgaagtacga | tgcgttcatg | aaggaactga | acggcactca | ttaccagggt | 2100 |
| gtcgtttggg | ccggtcccag | ttacttccct | gactggtttc | acccgaacgc | tcaggaatac | 2160 |

```
tggacggagc agttcctcaa cttcttcgac ggcgtcaacg gcccggacat tgatgccctg    2220
tggatcgaca tgaatgagcc cgccaacttt tataaccgcc cctacccagg caacaacacc    2280
accccggagg agtttgccga ggcgaatgac aaccccctg agccaccggc cgtgagggac     2340
gggccagatg cccctatccc cgggttcccg gatagtctcc agccaaactt cgcttctggc    2400
cagacaaacg agaagcgcgc agttgtcacc gtcgaacgtc gggctcggtc tcaatcgcac    2460
cgccagctcg gcgctggccg ctggcggtct gcagtccgcc actggccgcg agacccaaag    2520
gctggctggc agcacggccg caaatccggc tctggctgcg gccccacga gtgcagaggt     2580 ctgcccaacc gcgagctcat caggccgccg tatatgattc agaacggcgc cggcccaacg    2640
ctggcggaca cactgcggga cacggatatc gtgcaaagcg gcggatacgt ccagtacgac    2700
acgcacagcc tttacggcgc gatgatgtcc actcattcgc acaatgccat gcgggctaga    2760
cgtcccgatg accgcgcatt ggtgatcacc aggagcacat tgccggctc tggaaaggat     2820 gtctcgcact ggcttggagg taaggaattc ctgcaatcta aatttgcggc aaggggaac     2880 agctgctgac tagccctact tttctctgca gataacatct ccgattggct ttcataccga    2940
ctgtccatct cccagattct ccagttcgcc tcgctctacc agatcccgt tgtcggccct     3000 gatgtctgcg gcttcggtgg aaacgtaact gagaccctct gtgccaggta cgatcgccct    3060
aactcgacag catcttacgt gcctgctaac atagtctcta ctagatgggc taccctcggc    3120
tccttctaca ctttcttccg caaccacgcc gagatctttg ccaatcccca agagttctac    3180
cggtggccga tcgtcgccga agcggcccgc aacggcattg ccattcgata ccagctgcgt    3240
aagtctgcgt tcaccattag atcccaacat aattaacatt gagtccgcca atctagtcga    3300
ctacatttac acagccatct acaagcagac ccaaactggc acaccatccc ttaacccgct    3360
cttcttcaac taccccttcg accaaaacac ttacggcatc gatctccagt tcttctatgg    3420
ccccggcatc cttgtctctc cggtcacgga ggaaaacagc accagtgttt cctactacct    3480
tcccgacgac atcttctatg aatggggaac tggcaagccc gtccgcggac acggcgagta    3540
cgtctccgcc gaagtcgacg tcacccatat cacggtgcac tataagggcg gtctcgtcta    3600
tccacagcgg atcgagagcg cgaacaccac aactgcgctg cgccagaagg gattcaatat    3660
cgtcattgca ccgggcttgg atggctctgc tcatggagag ctttaccttg acgatggcct    3720
gtcgcaggtg caggataaag tctccgagat tgactttagc tatgtcgatg gcgtctttga    3780
gatgaagggc tcgtttgagt atgacccagg cgtcggaatc gagcggatta ctattctggg    3840
tgtgggggcc aagcccgagg tggcggctga ggacgcggag gtcgagtatg atgaggagaa    3900
tcagaagctg gtgctgcacg tcgatgtacc cttgacgcga aagtcaagta tcaagattgc    3960
ttgagtggga gggatggaat gacagggaga ggccatcaag ttgcttgctg cctacttagc    4020
ctagtcaggc ttggacgatt gcgcatacct ctggttaagg cagatgttcc ctgatcagtg    4080
gaggcaacca ttgccccccg ttcacttacc acttggatat gcccatggct ctaataggaa    4140
tacttaatcc taaataatac attattatga caatctccca aaacctattt ccggctgatg    4200
ataacgtgcc tggactccgt gcagctggaa tttgaataca acaaggagca ccgtgaagct    4260
atataagcct agagaaacta taagaatgct ggccttgtta cccttgtctc tgttcatagg    4320
tacggactca tgtgctgcta atagtcgact tactcatact tggcgcagat tattcataat    4380
cattgagtac ttactctatc gtaaggttgc tgatggagga cggttggcaa tgtggacgga    4440
gcttagagcg gcatggagaa agagctattt tatactagaa catatacaat ttgaaaaggt    4500
acaataagag gattataccca catttgcgcc ttgctcaata atacttcata ctatgtcctc    4560
```

```
ggcagtaggc cggagattaa tcataatatc tgcgacagac tattttcgag agagtgtagt    4620
ttgtactcga gaatgacatc tgctttaaaa aaagaaggac ttttctgaca gattagtgcc    4680
gggctactaa aggttctcga gccatatcga gtgtagttgg acgttttaca aatccgtaat    4740
gacgaaaaca cctgcagcaa cagtggatat ggccgtgctg atggagtttt gacgcaaaat    4800
gtctacgagg tatcactaat caatatagat ctcaaattgc ttttgtaccc atgctgtcgg    4860
ataatcctac cgcttagata tcagtaatac gtagccgcgg tagatacaag cgtatattat    4920
gcctgatatc ttaaggctga gaaacctaga aaggacctat tgccaagtta acgcatacag    4980
agaaaaacac gcggattcca ccatgtcaga cagaaagttg atccttgtta tgggaatact    5040
ggcgctcagg gcactcccgt tgtcaagggt acgtcgcatt ccagacggga ttgcgaggaa    5100
cagcagtcta acatggagaa tgatagccct ttcctcaagt ggccgctacg atgtccgagt    5160
actgactcga aataccgcct cagagcaggc taggaaaatg gttgtgctac ctcaggtaac    5220
gctccagcaa ggcttccagg aaaccaggca gatctccacg ctgccttcgc cagcgtatac    5280
ggcgcctgga cggctttacg ctcggggaaa aagcgagctg atctacggta tacgagcgta    5340
cgagatcgct cgtcatcatg gcgtcaaaca ctatgttttc gcgaatatcg actatactct    5400
ccgtaaagca ggttgggatg agcagtacca ttgcgcacat tgtgattcca aggcggattg    5460
gtgatctgat cctcaaccat ggccaggagg ggttcacagc tgagaccccg gccaggagtc    5520
ccgtatgatt actgtgctgc tgaccacggg gccgtacatg gatatgctct ttgatggaat    5580
gtttgtccca aggaaaaga ggatggttca tttgcttggg agaatccggc tggtaagctt    5640
```